(12) United States Patent
Robinson

(10) Patent No.: US 6,482,157 B2
(45) Date of Patent: Nov. 19, 2002

(54) ULTRASONIC DIAGNOSTIC IMAGING SYSTEMS WITH BLENDED MULTILINE FOR 2D AND 3D APPLICATIONS

(75) Inventor: Brent Stephen Robinson, Kirkland, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/823,022

(22) Filed: Mar. 30, 2001

(65) Prior Publication Data

US 2002/0143253 A1 Oct. 3, 2002

(51) Int. Cl.$^7$ ................................................. A61B 8/00
(52) U.S. Cl. ........................................................ 600/437
(58) Field of Search .............................. 600/447, 443, 600/441, 437, 454, 455, 449

(56) References Cited

U.S. PATENT DOCUMENTS 5,318,033 A * 6/1994 Savord
5,390,674 A * 2/1995 Robinson et al.
5,462,057 A * 10/1995 Hunt et al.
5,623,928 A * 4/1997 Wright et al.
5,678,552 A * 10/1997 Savord
5,779,640 A * 7/1998 Holley et al.
5,940,123 A * 8/1999 Daigle et al.
5,976,089 A   11/1999 Clark

* cited by examiner

*Primary Examiner*—Francis J. Jaworski
*Assistant Examiner*—Maulin Patel
(74) *Attorney, Agent, or Firm*—W. Brinton Yorks, Jr.

(57) ABSTRACT

Multiline acquisition is used to acquire groups of beams in response to transmit pulses. At least some of the beams from spatially adjacent groups are coaxially aligned. The echo information is detected and coaxially aligned beams are blended together using weighting functions which vary as a function of the time and location of the blended beams from their transmit beam apertures to gradually blend the aligned beams together spatially, thereby reducing multiline image artifacts. Echoes from moving objects in coaxially aligned beams may be aligned axially before the beams are blended together.

20 Claims, 8 Drawing Sheets

ULTRASONIC DIAGNOSTIC IMAGING SYSTEMS WITH BLENDED MULTILINE FOR 2D AND 3D APPLICATIONS

This invention relates to ultrasonic diagnostic imaging systems and, in particular, to ultrasonic diagnostic imaging systems which produce two dimensional (2D) and three dimensional (3D) blended multiline images.

Ultrasonic diagnostic imaging systems produce images of the interior of the body by transmitting ultrasonic waves which are steered and focused along transmit beam paths. Echoes are received from along the transmit beam path which are used to produce an image of the structure or motion encountered along the beam path. A number of adjacently transmitted beams and their echoes will interrogate a planar region of the body and the echoes can be used to produce a planar image of the body. The beams may also be transmitted adjacent to each other in three dimensions through a volumetric region, and the resulting echoes used to produce a three dimensional image of the volumetric region.

While the time required to insonify a planar region with transmit beams can be relatively short, enabling the production of 2D images of the planar region at a relatively rapid, real time rate, the time required to insonify a volumetric region can be significant. The governing factor on the time needed to insonify a volumetric region with multiple beams in three dimensions and to receive the echoes from along each of the transmit beam paths is the speed of sound, approximately 1540 m/sec. in the body. This latency is a serious limitation on the ability to perform real time, three dimensional ultrasonic imaging. An approach to addressing this limitation is to insonify the volumetric region with fewer transmit beams and to receive multiple receive beams in response to each transmit beam. This approach is known as multiline and requires a multiline beamformer which is capable of separately steering multiple receive beams in response to a single transmit beam. While multiline beamformers are in commercial use today, such beamformers typically only produce a small number of receive beams, two to six, in response to one transmit beam. Multiline beamformers for 3D imaging will need to be capable of high order multiline, where a dozen or more receive beams are produced in response to a transmit beam. The present invention is based upon the multiline technique and is especially suitable for high order multiline.

Multiline imaging is subject to several kinds of image artifacts, however. One type of artifact is the spatial artifact arising by reason of the nonuniform lateral characteristics of the insonifying transmit beams. While the beam characteristic can be made relatively flat near the beam center, the intensity rolloff at the lateral extremes of the transmit beam can affect the receive beams at those locations. While such artifacts can be removed fairly effectively for low order multiline (e.g., two receive beams for every transmit beam, or 2×multiline) by lateral spatial filtering, such filtering is unacceptable for high order multiline due to the low cut-off frequencies which result from the spatial periodicity of the greater number of receive beams.

The other type of artifact is temporal artifacts arising during imaging of moving tissue. This is always a problem during 3D cardiac imaging, and is especially noticeable at the seams of a multiline image where one group of multilines received from one transmit beam abuts another group of multilines received from an adjacent transmit beam. Accordingly it is desirable to be able to reduce these artifacts during multiline imaging, and particularly during multiline 3D imaging.

In accordance with the principles of the present invention groups of receive beams are received in response to the transmission of each of a plurality of transmit beams. Adjacent groups of receive beams spatially overlap and are detected and combined with weighting functions which vary in proportion to the spacing of a receive beam from its transmit beam. In accordance with a further aspect of the present invention, the receive beam signals are shifted in space or time prior to being combined. The inventive technique is applicable to both 2D and 3D ultrasonic imaging systems.

Figure 1A:
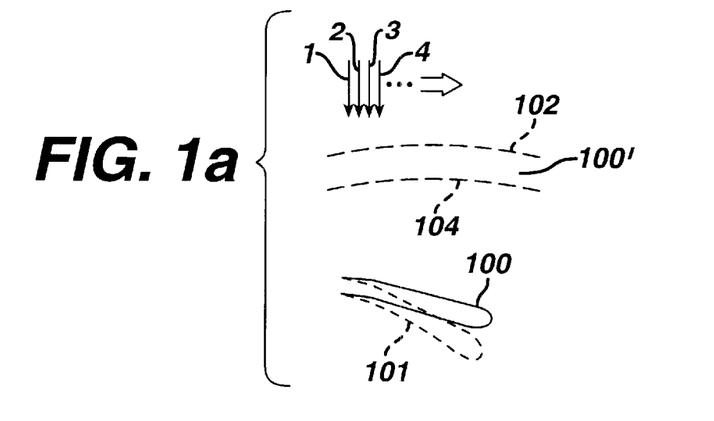
FIGS. 1*a* and 1*b* illustrate the effect of motion on conventional single line imaging and on multiline imaging.

FIG. 1*a* illustrates the effect of ultrasonic scanning of a moving object in the body by conventional single line imaging, such as a heart valve leaflet. In this illustration a sequence of transmit beams 1, 2, 3, 4, etc. are transmitted to scan the moving object 100. In response to each transmit beam a single receive beam is received which is coaxial with the transmit beam. The scanning sequence proceeds in the direction indicated by the arrow. A section 101' of the object is shown immediately below the transmit beams, and has an upper surface 102 and a lower surface 104. In this example (which is exaggerated for purposes of illustration) the object is moving downward during the scanning sequence. At the time of the first transmit beam the object may be in a position as shown at 100, but as the scanning sequence proceeds from left to right, each successive beam acquires echoes from the object when the object is at a slightly lower position due to its motion. When these echoes are assembled to form an image of the moving object, the object will appear in neither its starting position 100 or its ending position, but will be a distorted mix of the two, as indicated by the phantom 101. The left end of the object will appear in the position the left end was located at the time of beam 1, and the right end of the object will appear in the position the right end was located at the time of the last beam to interrogate that end. In between, the object will appear in successive locations of the times those sections were interrogated by the beams.

Figure 1B:
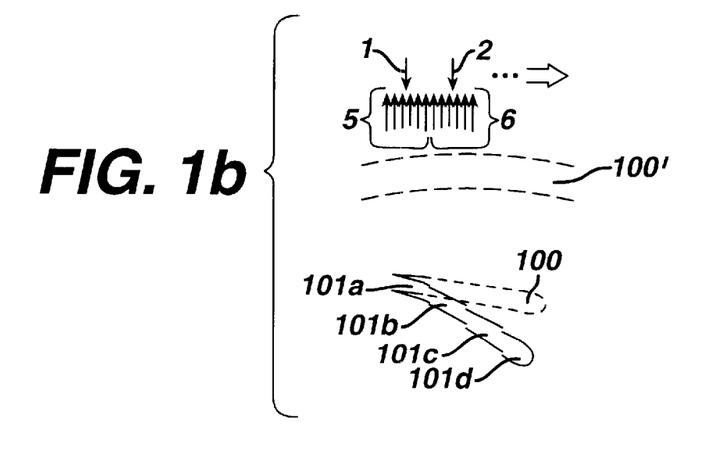

FIG. 1*b* illustrates the scanning of the same moving object 100 but by use of multiline reception. In this drawing each transmit beam 1, 2, etc. results in the reception of a group of six adjacent receive beams. Transmit beam 1 results in a group 5 of six receive beams, and transmit beam 2 results in a group 6 of six receive beams. This results in the scanning of consecutive sections of the object 100, since each transmit beam insonifies a section of the object at a discrete instant in time and location in its path of motion. Echoes are returned from the sections at their respective points in time and are used to form the adjacent receive beams. In this drawing the phantom 100 depicts the moving object at its location at the time of the first beam. Since the object is now captured in sectional lengths instead of a progression of time-sequential lines, the image of the object will appear as a disjointed group of sections 101a, 101b, 101c, and 101d. Such artifacts are readily visualized and are highly objectionable. Attempts to smooth over the mismatched jointures will usually result in blurring of the image at these locations and, in any event, such smoothing is not necessary if the targets are not in motion. This is a problem which is addressed by the present invention.

Figure 2:
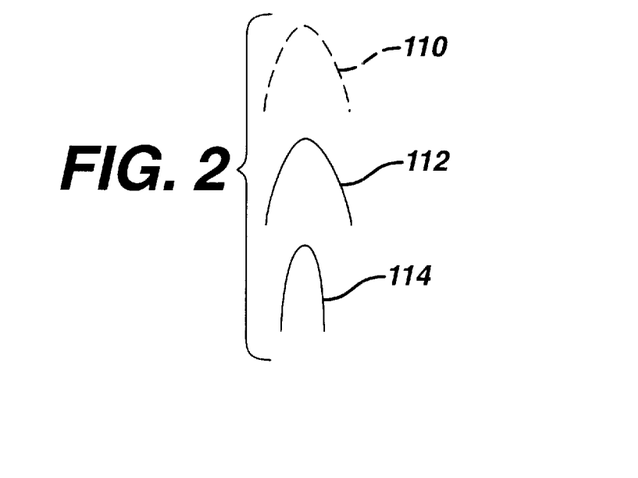
FIG. 2 illustrates beam profiles in conventional single line imaging.

FIG. 2 illustrates beam profiles of a transmit beam which results in a single coaxial receive beam. Profile 110 depicts the profile of a transmit beam and profile 112 depicts the profile of the resulting coaxial receive beam. The beams will result in a round-trip beam profile which is, to a useful approximation, a product of the transmit and receive beam profiles. Such a profile is shown at 114, which is seen to be narrower and hence of better lateral resolution than either the transmit or receive profile alone.

Figure 3:
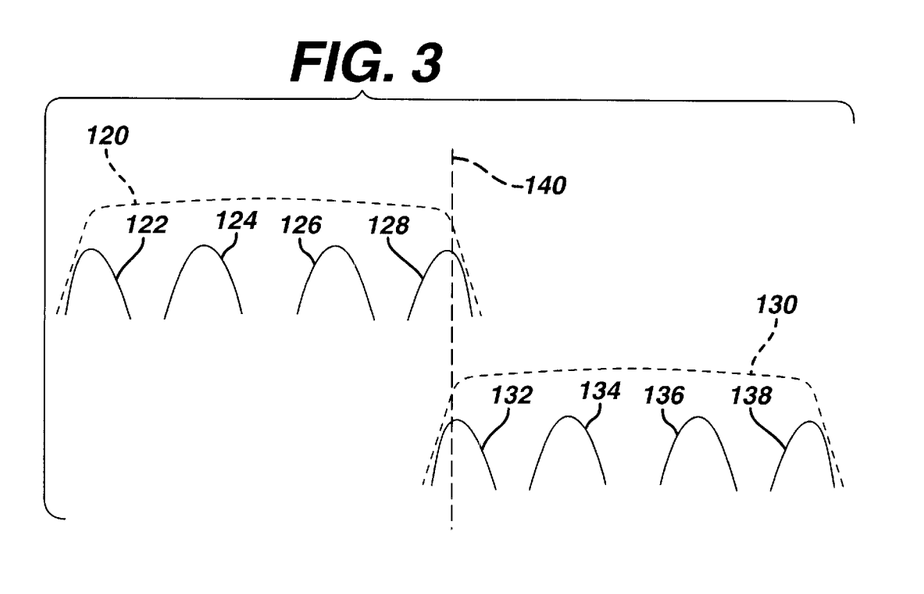
FIG. 3 illustrates beam profiles in multiline imaging.

FIG. 3 depicts beam profiles for multiline reception. In this case the transmit beam must insonify the locations of all of the spatially discrete multiple receive lines. Accordingly, the transmit beam profile 120 is broader than that of the single beam approach of FIG. 2. Such a broad profile is referred to herein as a "fat" beam, and refers to a beam profile encompassing the locations of three or more receive beams. In order to preserve as much sidelobe suppression as possible the fat beam profile is generally kept as narrow as possible, and usually is only as broad as required to insonify the receive beam locations substantially evenly. The receive beams are generally grouped symmetrically about the transmit beam center, as indicated by receive beam profiles 122, 124, 126 and 128 in FIG. 3 for a 4:1 multiline approach. However, at the lateral skirts of the transmit beam profile 120, the rolloff in energy can result in a cutoff or asymmetrical distortion of the most lateral beam profiles 122 and 128, with the more centrally located beams having more uniform, symmetrical profiles.

An approach which addresses this asymmetry is shown in the profiles of the adjacent group of multilines. This second group of multilines is identical to the first group, with a transmit beam profile 130 and receive beam profiles 132, 134, 136, 138, but is spatially shifted to the right so that receive beam profiles 128 and 132 of the two groups are spatially aligned as shown by broken line 140. Whereas receive beam profile 128 is distorted by the right skirt of its transmit beam profile, receive beam profile 132 is distorted by the left skirt of its transmit beam profile. As a result, the two receive beams with profiles 128 and 132 can be blended together to result in a beam with a symmetrical profile.

Figure 4:
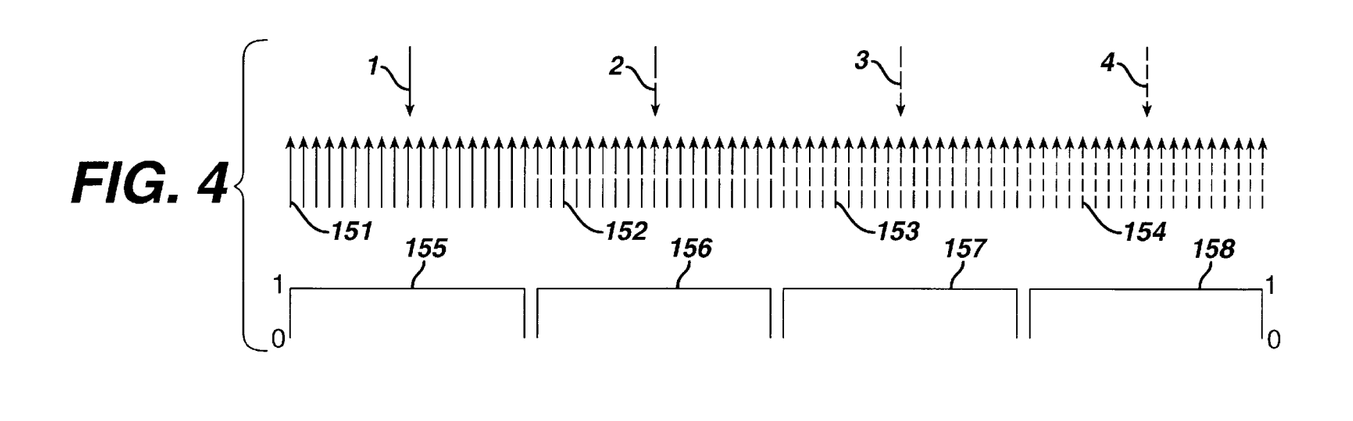
FIG. 4 illustrates multiline reception with no spatial overlap of received lines.

The application of these concepts to high order multiline is shown in FIG. 4, where a 19:1 multiline arrangement is depicted. The solid arrow 1 indicates the center of a fat transmit beam resulting in the reception of nineteen receive beams depicted by the solid arrows 151 pointing upward. Adjacent to this group of receive beams is a second group depicted by the two-segment arrows 152 which result from transmission of a fat beam centered about two-segment arrow 2. In a similar manner the group of receive beams depicted by three-segment arrows 153 result from fat transmit beam 3, and the group of receive beams depicted by four-segment arrows 154 result from fat transmit beam 4.

These beams fully cover an image field extending from the left-most beam 151 to the right-most beam 154 without overlap. Since there is no spatial overlap of the receive beams, they are used in equal measure to form the ultrasound image. The bars 155–158 below the receive beams indicate the weights to be used in weighting each receive beam in the image, with weighting factors on a scale of 0 to 1. In this case, with no overlapping beams, every beam is weighted with a weight of 1.

Figure 5:
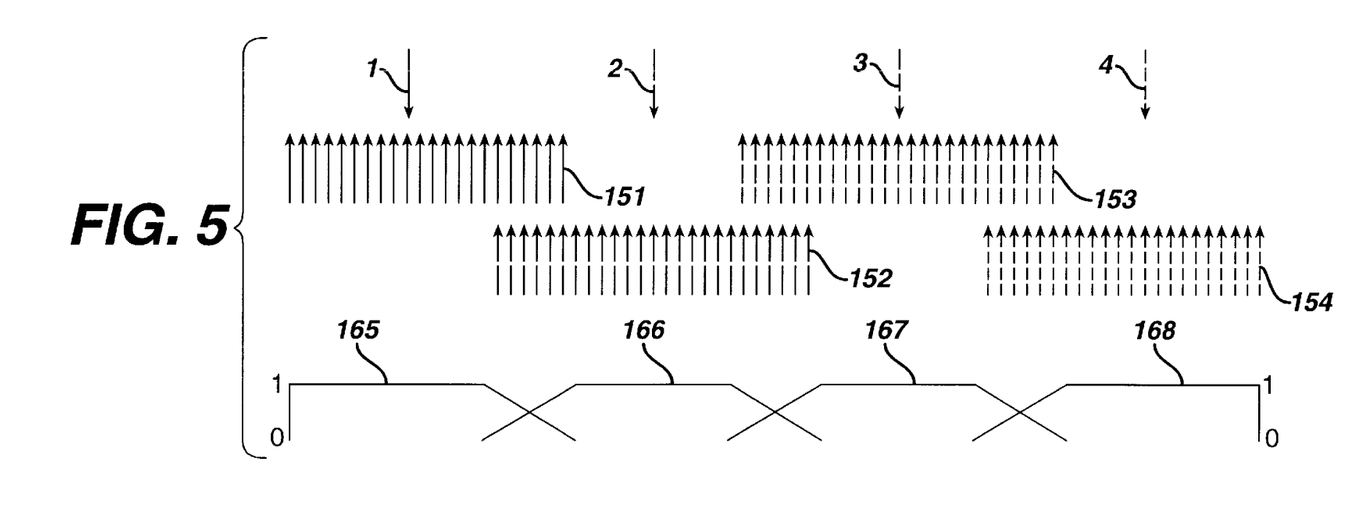
FIG. 5 illustrates multiline blending in accordance with a first embodiment of the present invention.

FIG. 5 depicts an embodiment of the present invention in which high order multiline groups overlap. In this illustration six beams of group 151 are spatially coaxially aligned with six beams of group 152, six beams of group 152 are spatially coaxially aligned with six beams of group 153, and six beams of group 153 are spatially coaxially aligned with six beams of group 154. The weighting factors for the receive beams are shown below the receive beam groups, with 165 representing the weighting factors applied to receive beams of group 151, 166 representing the weighting factors applied to receive beams of group 152, 167 representing the weighting factors applied to receive beams of group 153, and 168 representing the weighting factors applied to receive beams of group 154. As the drawing illustrates, where beams do not overlap each beam has a weight of 1. Where beams overlap the aligned beams are blended together by weighting factors that vary as a function of the proximity of the receive beam to the center of the transmit beam. For instance, proceeding from left to right through the last six receive beams of group 151, the weighting factor used for these beams progressively declines from just below 1 to almost 0. Correspondingly, proceeding from left to right through the co-aligned first six receive beams of group 152, the weighting factor used for these beams progressively increases from just above 0 to almost 1. The combined weights of the co-aligned beams will equal approximately 1, and are chosen to normalize signal levels when the co-aligned beams are weighted and combined, after taking into account possible fall-off in the transmit beam patterns. The weighting factors may thus not necessarily follow the linear progressions illustrated in FIG. 5. A similar blending of co-aligned beams occurs for each group of six overlapping receive beams.

Figure 6:
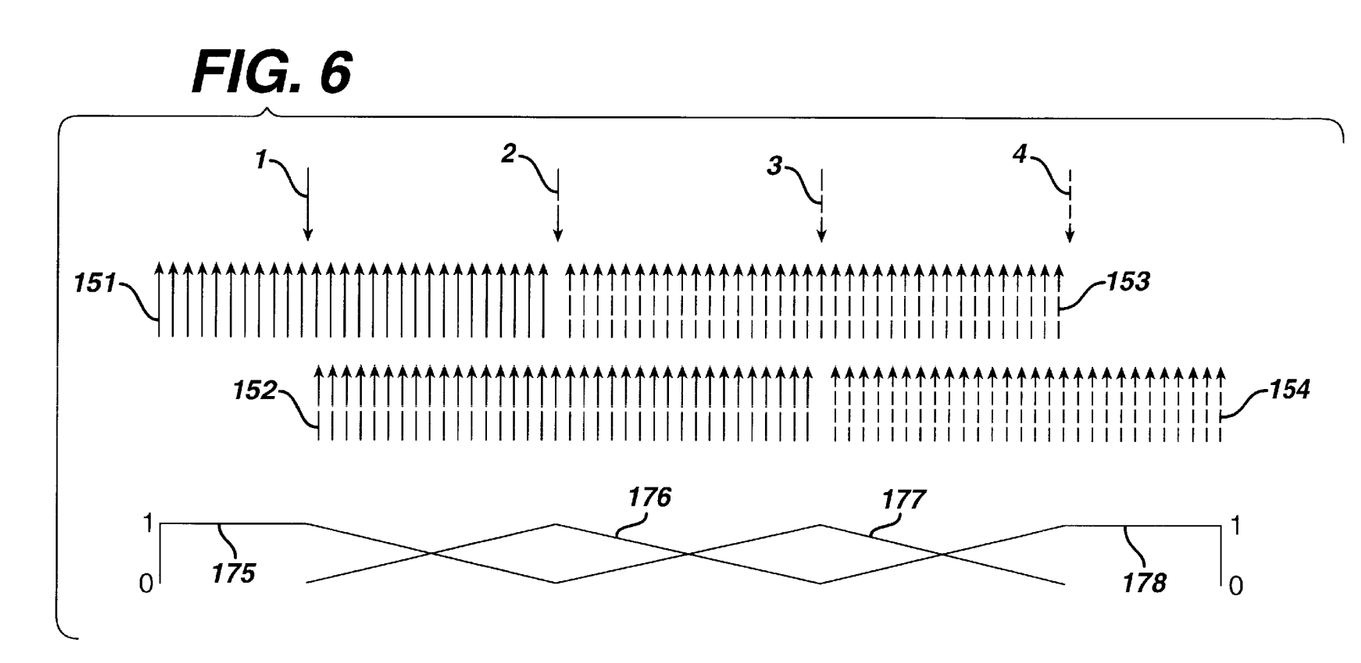
FIG. 6 illustrates multiline blending in accordance with a second embodiment of the present invention.

FIG. 6 extends this concept to the case where virtually every receive beam from one transmit beam is co-aligned with a receive beam from another transmit beam. In this drawing the lateral spacing of the transmit beams 1, 2, 3, and 4, and the spacing and order of the received beam groups 151, 152, 153, and 154 has been chosen such that virtually every receive beam from one group is aligned with a receive beam from another group. Thus, the weighting factors used will continuously change for the central groups 152 and 153, as shown by the continually changing weighting factor bars 176 and 177. The weights are held constant only where the beams do not overlap at the ends of groups 151 and 154 as shown by weighting factor bars 175 and 178. Over all but the peripheral regions of the image field the aligned receive beams are blended together with continually progressively changing weighting factors.

While the blending of the aligned multiline receive beams can be performed on the rf receive signals, which performs well in the absence of any motion in the image field, it is preferred that the blending be done with incoherent signals, that is, post-detection. This is because moving targets can result in random signal cancellation due to the phase difference of the echo signals being combined. Moreover, even the smallest movement can cause signal cancellation. For instance a 125 $\mu$m phase shift or difference between echoes will result in almost complete cancellation of a 3 MHz ultrasound signal. This means that ⅛ of a millimeter of motion between pulses will cause cancellation and signal dropout in the image. Envelope detection before combining eliminates these phase difference dropout effects.

Figure 7:
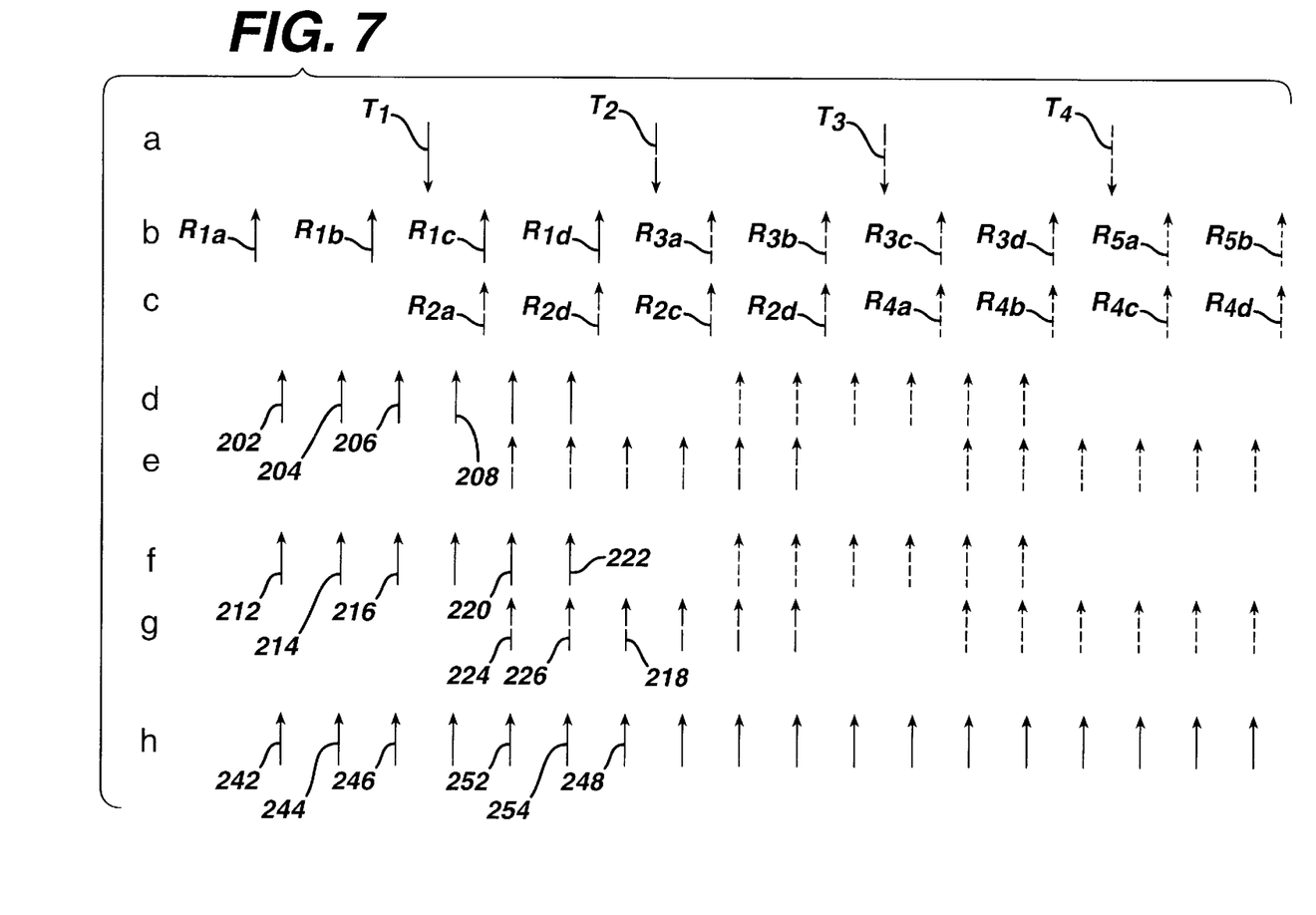
FIG. 7 illustrates multiline blending in accordance with the present invention with coherent lateral interpolation.

FIG. 7 shows another embodiment of the present invention which uses both multiline blending and lateral interpolation. Since a group of multiline beams received from a single transmit beam result from a single transmit event, there are no temporal effects between the receive beams of the multiline group. Thus, a group of multiline receive beams exhibit no beam-to-beam motional effects. Accordingly, inter-group interpolation can be performed without causing the motion artifacts and dropout effects described above; any differences are only due to the spatial aperture differences between the receive beams. The embodiment of FIG. 7 takes advantage of this property to increase the receive line density before multiline blending. In the drawing, transmit beams $T_1$, $T_2$, $T_3$, and $T_4$ shown across line 7a are used in a 4:1 multiline arrangement, with transmit beam $T_1$ producing four receive beams $R_{1a}$, $R_{1b}$, $R_{1c}$, and $R_{1d}$ as shown in line 7b. Similarly, transmit beam $T_2$ produces four receive beams $R_{2a}$, $R_{2b}$, $R_{2c}$, and $R_{2d}$ as shown in line 7c, and so forth. The four coherent receive beams produced in response to each transmit beam are then laterally interpolated as shown in lines 7d and 7c, using a ¼:¾ interpolation weighting as described in my U.S. Pat. No. 5,940,123. An interpolated beam 202 is formed by interpolating ($¾R_{1a}+¼R_{1b}$), and an interpolated beam 204 is formed by interpolating ($¼R_{1a}+¾R_{1b}$). This rf interpolation technique is used to produce the interpolated beams drawn in lines 7d and 7e, thereby doubling the image line density from that of the multiline density.

The signals of the beams on lines 7d and 7e then undergo detection and, if desired, log compression to form the spatially corresponding beams shown on lines 7e and 7f. Spatially aligned beams are then blended together to form the image lines shown on line 7h. Image lines 242, 244, 246, and 248 are the same as beams 212, 214, 216 and 218 as there are no overlapping beams in these parts of the image field. However image lines 252 and 254 which spatially correspond to multiple aligned beams are formed by blending detected signals from lines 7f and 7g. Due to the proximity of beams 220, 222, 224 and 226 to their respective transmit beam centers $T_1$, and $T_2$, a ¼:¾ weighting for these blended image lines is used. Thus, image line 252 is equal to ¾(beam 220)+¼(beam 224), and image line 254 is equal to ¼(beam 222)+¾(beam 226). Alternatively the blend could be made more gradual and weights of ⅔(beam 220)+⅓(beam 224) could be used to produce image line 252, and so on.

Figure 8:
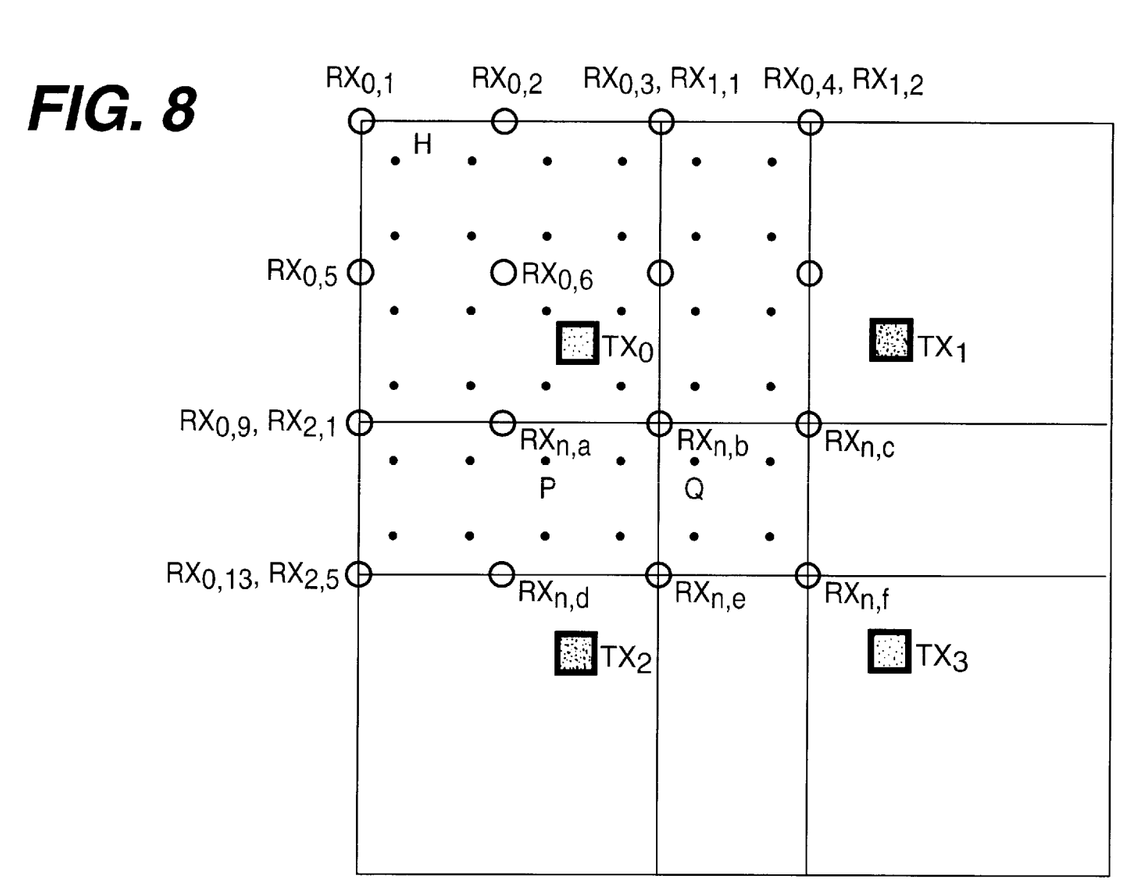
FIG. 8 illustrates multiline blending in three dimensional imaging in accordance with the principles of the present invention.

FIG. 8 illustrates an embodiment of the present invention in three dimensional imaging of a volumetric region. In this drawing the volumetric region has two dimensions in the plane of the drawing, and the third dimension is normal to the plane of the drawing. The transmit and receive beams are viewed axially in the drawing, with the shaded squares representing the centers of four transmit beams $TX_0$, $TX_1$, $TX_2$, and $TX_3$. Each transmit beam produces sixteen receive beams, or 16:1 multiline. The sixteen receive beams from transmit beam $TX_0$ are arrayed in four rows of four beams, starting with receive beams $RX_{0,1}$ through $RX_{0,4}$ in the top row and continuing through receive beams $RX_{0,13}$ through $RX_{n,f}$ in the fourth row, where the first subscript indicates the transmit beam number and the second subscript represents the receive beam for that transmit beam. The transmit beams are laterally spaced in two dimensions by a two-receive beam spacing, resulting in the eight receive beams on each side of a transmit beam location overlapping with eight receive beams of the adjacent transmit beam. This further results in the overlap of four receive beams in any region bounded by a perimeter of transmit beam locations. Thus, the eight receive beams $RX_{0,9}$ through $RX_{0,16}$ of transmit beam $TX_0$ are aligned with the eight receive beams $RX_{2,1}$ through $RX_{2,8}$ of transmit beam $TX_2$. Receive beams from each of the transmit beams $TX_0$, $TX_1$, $TX_2$, and $TX_3$ are aligned at receive beam locations $RX_{n,b}$, $RX_{n,c}$, $RX_{n,e}$, and $RX_{n,f}$.

As in the previous example, rf (coherent) interpolation is used with temporally identical receive beams, that is, beams from the same multiline group, and temporally different beams are blended after detection. This may be illustrated by the combinations and weights used to develop receive image lines at locations P and Q in the volume. For image line P, receive lines from transmit beam $TX_0$ are combined by coherent interpolation as follows:

$$P_0=0.75(0.75RX_{0,a}+0.25RX_{0,b})+0.25(0.75RX_{0,d}+0.25RX_{0,e})$$

Receive lines from transmit beam $TX_2$ are combined coherently by:

$$P_2=0.75(0.75RX_{2,a}+0.25RX_{2,b})+0.25(0.75RX_{2,d}+0.25RX_{2,e})$$

After detection these lines are blended to produce an image line for P by:

$$P=0.75P_0+0.25P_2$$

Thus, image line P is formed from echoes from two transmit beams.

An image line Q, however, being surrounded by four transmit beam locations, is formed from echoes from those four transmit beams. After four-point coherent interpolation of temporally common beams from the same transmit beam is used to produce $Q_0$, $Q_1$, $Q_2$, and $Q_3$ (in the same manner of $P_0$ and $P_2$ above), interpolation of these temporally different results would result in:

$$Q=0.75(0.75Q_0+0.25Q_1)+0.25(0.75Q_2+0.25Q_3)$$

The averaging inherent in blending multiline receive beams reduces multiline artifacts. Spatial artifacts are reduced because beams with different spatial characteristics are averaged together. Temporal artifacts are reduced because the temporal discontinuities that occur at the edges of the multiline bundles are reduced by averaging between the echoes received from a particular direction at one time and the echoes received from the same direction at a different time. The key to successful blending is to have a gradual transition between the weights applied to different lines, as shown in FIGS. 5 and 6. Multiline blending applies the heaviest averaging at the edges of the multiline bundles, precisely in the regions where the artifacts are the worst.

In higher order, fat transmit beam multiline, the transmit beam contributes virtually nothing to spatial resolution and so, effectively, only the receive beams (acquired or synthesized) are averaged. Since the receive beams are coincident and substantially similar, the filtering is largely temporal rather than spatial and consequently multiline artifacts can be suppressed while spatial resolution is largely preserved.

Figure 9:
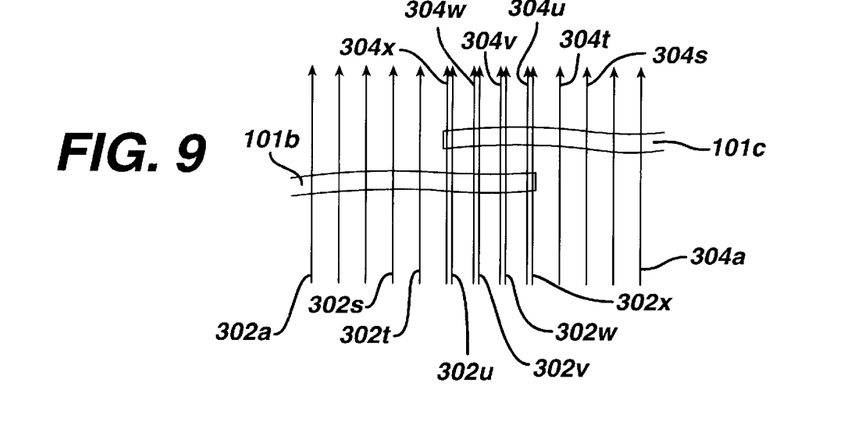
FIGS. 9–11 illustrates multiline blending in accordance with the present invention with weighted time shifting of blended signals.
Figure 10:
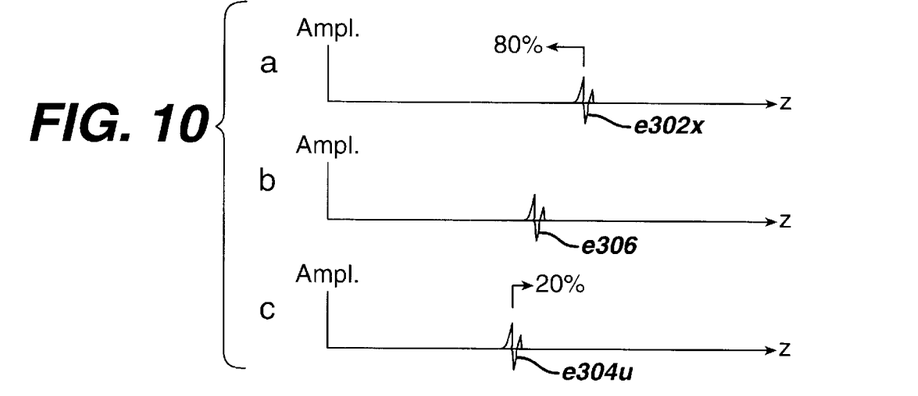

As FIG. 1b demonstrates, multiline artifacts from motion arise due to the differing spatial location of a moving object when it is interrogated by a temporally different transmit beam. When the object is moving toward or away from the transducer co-located receive beams from different transmit beams will exhibit echoes at slightly different locations along the receive beams, that is, the times of reception of the echo from the moving object will be slightly different. This is demonstrated in FIG. 9, where a moving object is moving upward toward the transducer. A transmit beam which acquires receive beams 302a . . . 302s, 302t, 302u, 302v, 302w, and 302x will return echoes from the moving object which appears to be located as shown by object section 101b. A later transmit beam which acquires receive beams 304a . . . 304s, 304t, 304u, 304v, 304w, and 304x will return echoes from the moving object which appears to be located as shown by object section 101c. Four beams of each group are overlapping: receive beams 302u, 302v, 302w and 302x are aligned with receive beams 304x, 304w, 304v and 304u, respectively. The echoes received on the aligned beams 302x and 304u are shown in time and depth z relation in FIG. 10. FIG. 10a shows the echo e302x received from the object by beam 302x when the object was at position 101b. The echo e302x occurs at a given depth z (time) along the beam 302x. FIG. 10c shows the echo e304u received from the object by beam 304u at a later time when the object was at position 101c. In comparison with echo e302x, the echo e304u is at a shallower depth z (earlier receive time) along the beam 304u. In accordance with a further aspect of the present invention, in addition to blending these echoes, they may be both time-shifted to bring them into an intermediate time alignment before blending. In this embodiment the time-shifting is related to the proximity of the receive beams from their respective transmit beam centers. Receive beam 302x, being more greatly removed from its transmit beam than 304u is removed from its transmit beam, has its echo e302x shifted toward the time (depth) of echo e304u by 80% of the time (depth) distance between the two echoes. Similarly, since receive beam 304u is closer to its transmit beam than receive beam 302x is to its transmit beam, the echo e304u is shifted toward echo e302x by 20% of the time (depth) between the two echoes. The time shifted echoes are then blended by weighting factors which are a function of the proximity of the receive beams from the transmit beams (0.80 for echo e304u and 0.20 for echo e302x) to produce a blended echo signal e306 at the depth (time) location on a blended receive beam as shown in FIG. 10b.

Figure 11:
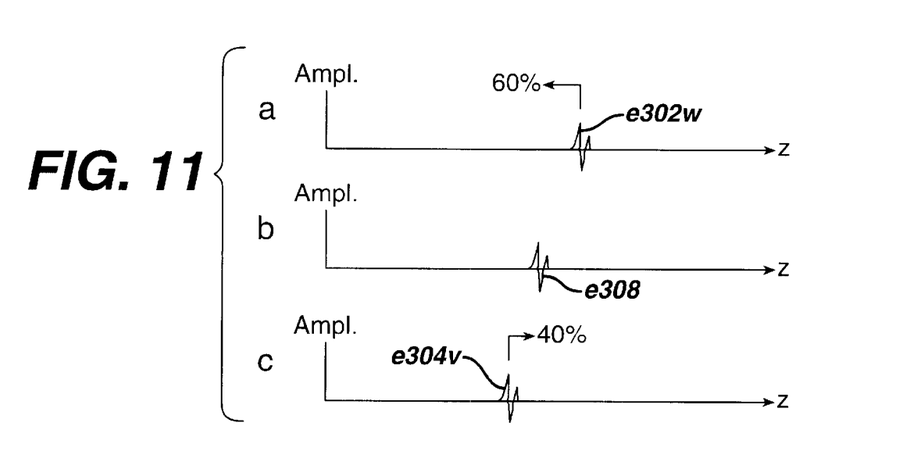

This same blending technique is performed using the other overlapping beams. FIG. 11 shows the operation for aligned receive beams 302w and 304b. Applying the same time shifting and blending weighting rationale, the echo e302w is time shifted 60% of the time (depth) disparity between echoes e302w and e304v toward echo e304v as shown in FIG. 11a. The echo e304v on receive beam 304v is time shifted 40% of the distance (time) disparity toward echo e302w as shown in FIG. 11c. The shifted echo e304v is weighted by 0.60 and the shifted echo e302w is weighted by 0.40 to produce a blended echo e308 at an intermediate position (time) on the blended receive beam as shown in FIG. 11b. The same time shifting and weighting criteria are applied to aligned beams 302v,304x and 302u,304xto produce blended beams at those locations also. It is thus seen that the illustrated weighting criteria result in greater time shifting and lesser weighting of beams more greatly distant from their transmit beam centers than beams which are closer to their transmit beam centers. If desired the identification of moving objects along a beam location can be sensed by Doppler interrogation along the beam location. Alternatively motion can be sensed by feature recognition performed on detected multiline groups prior to multiline blending. Lateral as well as axial motion can be compensated by the inventive techniques.

Figure 12:
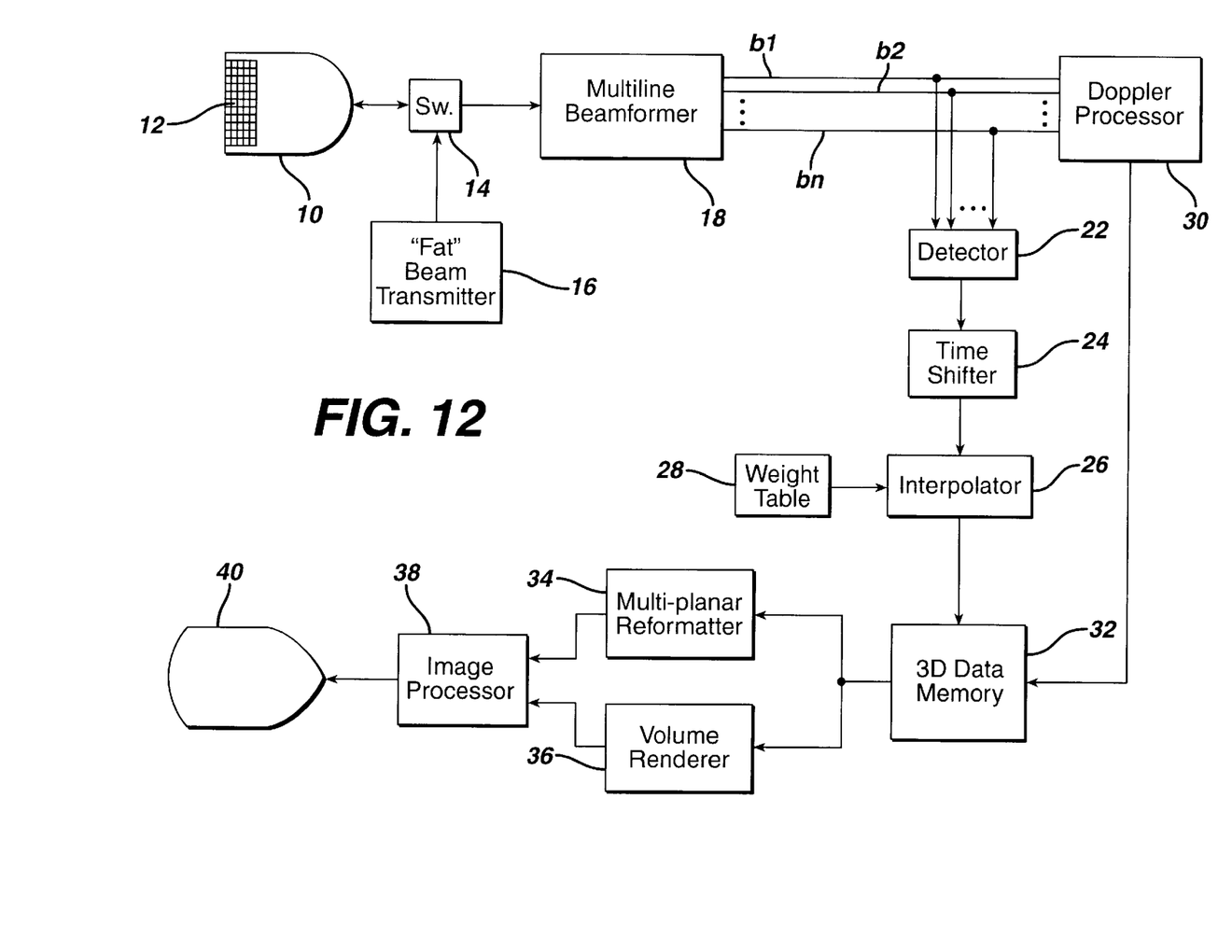
FIG. 12 illustrates an ultrasonic diagnostic imaging system constructed in accordance with the principles of the present invention.

FIG. 12 illustrates an ultrasound system constructed to perform multiline blending in accordance with the present invention. An ultrasonic probe 10 capable of three dimensional imaging includes a two dimensional array 12 which transmits fat beams over a three dimensional volume and receives multiple receive beams in response to each transmit beam. Suitable two dimensional array are described in U.S. patent application Ser. No. 09/663,357 and in U.S. patent application Ser. No. 09/645,872. The transmit beam characteristics of the array are controlled by a "fat" beam transmitter 16, which causes the elements of the array to emit a focused beam of the desired breadth in a desired direction through a volumetric region of the body. Transmit pulses are coupled from the transmitter 16 to the elements of the array by means of a transmit/receive switch 14. The echo signals received by the array elements in response to a transmit beam are coupled to a multiline beamformer 18, where the echo signals received by the elements of the array transducer are processed to form multiple receive beams in response to a transmit beam. A suitable multiline beamformer for this purpose is described in U.S. patent application Ser. No. 09/746,165. Rather than housing all of the beamformer circuitry in the system beamformer 18, the beamformer circuitry may be distributed between the probe 10 and the system as described in U.S. patent application Ser. No. 09/645,872.

The multiple receive beams formed by the multiline beamformer are shown located on separate beamformer output lines b1, b2, . . . bn, but may be time-interleaved on fewer than n output lines if desired. The multiple receive beams are coupled to a Doppler processor 30, which processes the echo information into Doppler power or velocity information. The three dimensional Doppler information is stored in a 3D data memory 32, from which it can be displayed in various formats such as a 3D power Doppler display as described in U.S. Pat. No. Re. 36,564. The 3D data memory may comprise any memory device or group of memory devices which has three address parameters. The multiple receive beams are also coupled to a detector 22, where the echo signals are envelope detected. The detected echo signals may then be time-shifted along the receive beams as discussed in conjunction with FIGS. 9–11 above in a time shifter 24. Aligned receive beams are then blended in an interpolator 26, which applies weighting functions stored in a weight table 28. The blended signals as well as unblended signals for lines containing only a single receive beam are stored in the 3D data memory 32.

The three dimensional image data stored in the 3D data memory may be processed for display in several ways. One way is to produce multiple 2D planes of the volume. This is described in U.S. patent application Ser. No. 09/641,306. Such planar images of a volumetric region are produced by a multi-planar reformatter 34. The three dimensional image data may also be rendered to form a 3D display by a volume renderer 36. The resulting images are coupled to an image processor 38, from which they are displayed on an image display 40.

Numerous variations of the illustrated embodiments of the present invention are also possible. The blending of multiline image data described above can be performed on partially overlapped bundles of receive lines as shown in FIGS. 5 and 7–9. Alternatively blending can be performed on fully overlapped bundles of receive lines as shown in FIG. 6. It is also possible to blend more than two aligned lines by receiving three or more aligned lines at an image location from three or more transmit beams. Lateral rf interpolation is not necessary in a particular embodiment. In FIG. 6 lateral interpolation is shown being used to increase the line density, but this can also be accomplished by increasing the number of receive beams in a multiline group, i.e., the multiline order. The reason for interpolating or increasing the order of the multiline is so that the blend can be made more gradual across the region of overlapping beams.

An implementation of the present invention can be applied to hexagonal or other sampling patterns as well as the rectangular sampling grid illustrated. Dynamic oversteering of the receive beams can be used to ensure that the round-trip beams are fully spatially coincident. Blending beams which are adjacent although non-coincident will result in blended signals exhibiting poorer resolution than is the case with aligned receive beams. Such artifacts could be diminished somewhat by laterally filtering the blended image data. A short kernel filter can be used for this purpose.

The weights used for blending do not have to vary in the linear fashion depicted in the illustrated embodiments. The weights are preferably chosen to minimize the amount of spatial and/or temporal artifacts and, depending upon the multiline acquisition strategy employed and the intended clinical application, may use non-linear kernels. The blending does not have to be linear. Non-linear and/or adaptive combinations may also be used.

What is claimed is:

1. A method of reducing artifacts in ultrasonic images produced by multiline echo reception comprising:

transmitting a first transmit beam and receiving multiple spatially discrete beams in response;

transmitting a second transmit beam within the same image scanning sequence as that of the first transmit beam and receiving multiple spatially discrete beams in response, wherein a plurality of the beams received in response to the second transmit beam spatially correspond to beams received in response to the first transmit beam;

detecting the signals of the spatially corresponding beams; and blending together the signal information from the corresponding beams.

2. The method of claim 1, wherein blending includes weighting the signal information which is being blended.

3. The method of claim 2, wherein weighting comprises weighting the signal information as a function of the position of the received beam from a transmit beam, wherein overlapping groups of received beams are blended together in a spatially gradual fashion.

4. A method of reducing artifacts in ultrasonic images produced by multiline echo reception comprising:

transmitting a first transmit beam and receiving multiple spatially discrete beams in response;

transmitting a second transmit beam and receiving multiple spatially discrete beams in response, wherein a plurality of the beams received in response to the second transmit beam spatially correspond to beams received in response to the first transmit beam;

detecting the signals of the spatially corresponding beams; and blending together the signal information from the corresponding beams, wherein blending includes weighting the signal information which is being blended, wherein weighting comprises weighting the signal information as a function of the position of the received beam from a transmit beam, wherein overlapping groups of received beams are blended together in a spatially gradual fashion, wherein weighting further comprises weighting the signal information as a function of the position of the received beam from the center of a transmit beam.

5. The method of claim 3, wherein weighting comprises using a lesser weighting function for a received beam more greatly removed spatially from its transmit beam than the weighting function used for a received beam which is spatially closer to its transmit beam.

6. The method of claim 5, wherein the weighting functions are normalized.

7. The method of claim 1, wherein transmitting comprises transmitting a fat beam which insonifies the locations of beams to be received in response to the transmitted beam.

8. The method of claim 1, wherein the received beams of each transmit beam are distributed in two directions on either side of the transmit beam.

9. The method of claim 1, wherein the received beams of each transmit beam are distributed in three dimensions around the transmit beam.

10. The method of claim 1, wherein blending produces a more symmetrical beam profile than those of the beams being blended.

11. A method of reducing artifacts in ultrasonic images produced by multiline echo reception comprising:

transmitting a first transmit beam and receiving multiple spatially discrete beams in response;

transmitting a second transmit beam and receiving multiple spatially discrete beams in response, wherein a plurality of the beams received in response to the second transmit beam spatially correspond to beams received in response to the first transmit beam;

rf interpolating multiple beams received in response to a transmit beam to increase the beam density;

detecting the signals of the interpolated, spatially corresponding beams; and blending together the signal information from the corresponding beams.

12. The method of claim 11, wherein rf interpolating comprises lateral interpolation of temporally identical received beams; and wherein blending comprises combining spatially corresponding received beams.

13. The method of claim 12, wherein blending comprises combining weighted and spatially corresponding received beams.

14. The method of claim 13, wherein blending comprises combining spatially aligned received beams which are weighted as a function of both time and position from the transmit beam which produced the received beams.

15. A method of reducing artifacts in ultrasonic images produced by multiline echo reception comprising:

transmitting a first transmit beam and receiving multiple spatially discrete beams in response;

transmitting a second transmit beam within the same image scanning sequence as that of the first transmit beam and receiving multiple spatially discrete beams in response, wherein a plurality of the beams received in response to the second transmit beam are spatially aligned with beams received in response to the first transmit beam;

detecting the signals of the spatially aligned beams; and blending together the signal information from the spatially aligned beams.

16. The method of claim 15, further comprising time-shifting echo signals of aligned beams which result from moving objects, wherein the amount of time shifting is a function of the time or depth disparity between echoes of aligned beams which result from moving objects.

17. The method of claim 16, wherein the amount of time shifting is further a function of the location of an aligned beam from its transmit beam.

18. A method for ultrasonically imaging a three dimensional region comprising:

transmitting a plurality of spatially displaced fat transmit beams;

receiving a group of temporally identical but spatially discrete receive beams in response to each transmit beam, wherein the receive beams of a first group overlap the receive beams of a second group;

detecting echo signals in the overlapping receive beams;

blending together in a spatially varying manner the overlapping receive beams; and producing a volumetric display from the received and blended beams.

19. The method of claim 18, wherein producing comprises producing a volume rendering of received and blended beam information.

20. The method of claim 18, wherein producing comprises producing a plurality of multiplanar reformatted images from received and blended beam information.

* * * * *